United States Patent
Urade et al.

(10) Patent No.: US 10,005,964 B2
(45) Date of Patent: *Jun. 26, 2018

(54) PROCESS FOR CONVERTING A BIOMASS MATERIAL

(71) Applicant: SHELL OIL COMPANY, Houston, TX (US)

(72) Inventors: Vikrant Nanasaheb Urade, Bangalore (IN); Alan Anthony Del Paggio, Spring, TX (US); Laxmi Narasimhan Chilkoor Soundararajan, Bangalore (IN); Madhusudhan Rao Panchagnula, Bangalore (IN)

(73) Assignee: SHELL OIL COMPANY, Houston, TX (US)

( * ) Notice: Subject to any disclaimer, the term of this patent is extended or adjusted under 35 U.S.C. 154(b) by 26 days.

This patent is subject to a terminal disclaimer.

(21) Appl. No.: 14/758,620

(22) PCT Filed: Dec. 19, 2013

(86) PCT No.: PCT/EP2013/077547
§ 371 (c)(1),
(2) Date: Jun. 30, 2015

(87) PCT Pub. No.: WO2014/102156
PCT Pub. Date: Jul. 3, 2014

(65) Prior Publication Data
US 2015/0337215 A1    Nov. 26, 2015

(30) Foreign Application Priority Data
Dec. 31, 2012  (IN) .......................... 5515/CHE/2012

(51) Int. Cl.
*C12P 7/40* (2006.01)
*C10G 3/00* (2006.01)
(Continued)

(52) U.S. Cl.
CPC ............... *C10G 3/42* (2013.01); *C10G 3/44* (2013.01); *C10G 3/47* (2013.01); *C10G 3/49* (2013.01);
(Continued)

(58) Field of Classification Search
None
See application file for complete search history.

(56) References Cited

U.S. PATENT DOCUMENTS

| 5,962,307 A | 10/1999 | Holtzapple et al. |
| 6,043,392 A * | 3/2000 | Holtzapple ........... C07C 29/145 44/385 |
| 2008/0280338 A1 | 11/2008 | Hall et al. |

FOREIGN PATENT DOCUMENTS

| CN | 102292310 | 3/2014 |
| WO | 2010053681 | 5/2010 |

(Continued)

OTHER PUBLICATIONS

Sugioka et al., Studies in Surface Science and Catalysis 105: 1995-2001 (1997).*

(Continued)

*Primary Examiner* — Erin M. Bowers

(57) ABSTRACT

A process for converting a biomass material comprising a) converting a biomass material in one or more steps into one or more C3-C12 oxygenates; b) contacting the one or more C3-C12 oxygenates with hydrogen at a hydrogen partial pressure of more than 1.0 MegaPascal in the presence of a sulphided carbon-carbon coupling catalyst; wherein the carbon-carbon coupling catalyst comprises equal to or more than 60 wt % of a zeolite and in the range from equal to or more than 0.1% wt to equal to or less than 10 wt % of a hydrogenation metal, based on the total weight of the carbon-carbon coupling catalyst.

7 Claims, 1 Drawing Sheet

(51) Int. Cl.
  *C10L 1/04*  (2006.01)
  *C12P 7/52*  (2006.01)
  *C12P 7/54*  (2006.01)
  *C12P 39/00* (2006.01)

(52) U.S. Cl.
  CPC .................. *C10G 3/50* (2013.01); *C10L 1/04* (2013.01); *C12P 7/40* (2013.01); *C12P 7/52* (2013.01); *C12P 7/54* (2013.01); *C12P 39/00* (2013.01); *C10G 2300/1011* (2013.01); *C10L 2200/043* (2013.01); *C10L 2200/0438* (2013.01); *C10L 2200/0446* (2013.01); *C10L 2290/26* (2013.01); *Y02P 30/20* (2015.11)

(56) References Cited

FOREIGN PATENT DOCUMENTS

| WO | 2010065643 |   | 6/2010 |
|----|------------|---|--------|
| WO | WO 2010/065643 | * | 6/2010 |

OTHER PUBLICATIONS

Xu et al., "From Zeolites to Porous MOF Materials—the 40th Anniversary of International Zeolite Conference", Proceedings of the 15th International Zeolite Conference, Elsevier, 2007.*

Wikipedia, https://en.wikipedia.org/wiki/Vacuum, accessed Mar. 16, 2017.*

Vasquez S.T.; "Transformation of Acetone and Isopropanol to Hydrocarbons Using HZSM-5 Catalyst"; Graduate Studies of the Texas A&M University, USA; 2009.

Gayubo et al.; "Transformation of Oxygenate Compaonents of Biomass Pyrolysis Oilon a HZSM-5 Zeolite. i. Alcohols and Phenols"; Ind. Eng. Chem. Res.; vol. 43, pp. 2610-2618; 2004.

Gayubo et al.; "Transformation of Oxygenate Components of Biomass Pyrolysis Oil on a HZSM-5 Zeolite. II. Aldehydes, Ketones, and Acids"; Ind. Eng. Chem. Res.; vol. 43; pp. 2619-2626; 2004.

Agbogbo et al; "Recent advances in the MixAlco process for the production of mixed alcohol fuel"; ISAF XV Conference at San Diego, California; Sep. 26-28, 2005.

Aiello-Mazzarri et al; "Conversion of municipal solid waste to carboxylic aids using a mixed culture of mesophilic microorganisms"; Bioresource Technology 97; pp. 47-56; 2006.

* cited by examiner

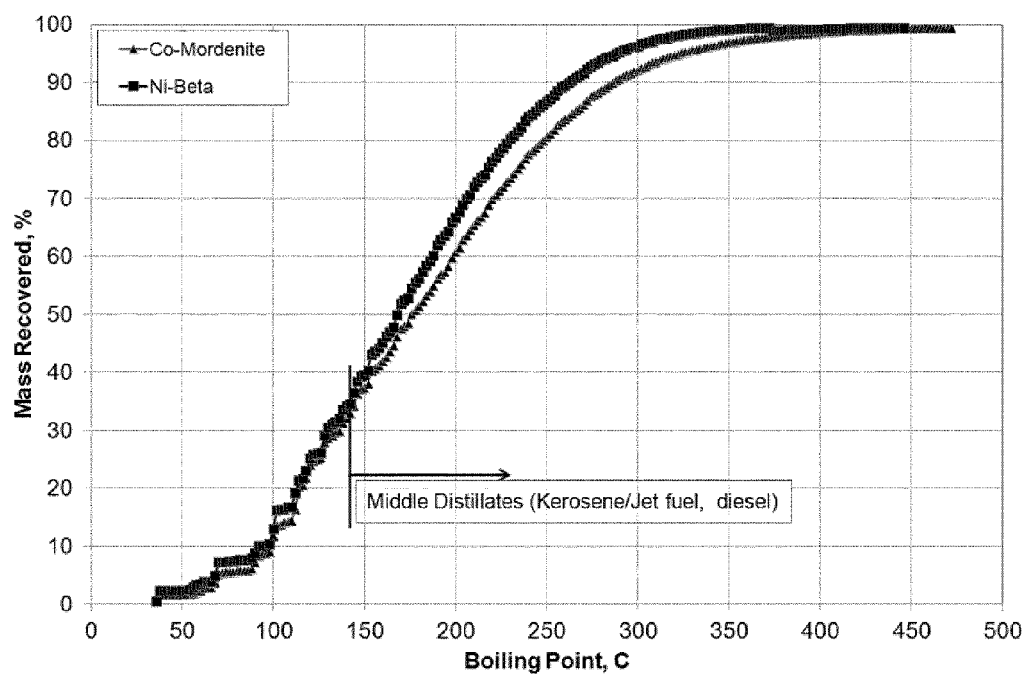

PROCESS FOR CONVERTING A BIOMASS MATERIAL

PRIORITY CLAIM

The present application is the National Stage (§ 371) of International Application No. PCT/EP2013/077547, filed Dec. 19, 2013, which claims priority from India Patent Application No. 5515/CHE/2012, filed Dec. 31, 2012 incorporated herein by reference.

FIELD OF THE INVENTION

This invention relates to a process for converting a biomass material. More specifically this invention relates to a process for converting a biomass material into a middle distillate boiling product.

BACKGROUND OF THE INVENTION

With increasing demand for liquid transportation fuels, decreasing reserves of 'easy oil' (crude petroleum oil that can be accessed and recovered easily) and increasing constraints on carbon footprints of such fuels, it is becoming increasingly important to develop routes to produce liquid transportation fuels from biomass in an efficient manner. Such liquid transportation fuels produced from biomass are sometimes also referred to as biofuels. Biomass offers a source of renewable carbon. Therefore, when using such biofuels, it may be possible to achieve more sustainable $CO_2$ emissions over petroleum-derived fuels.

In the paper titled "Recent advances in the MixAlco process for the production of mixed alcohol fuel" presented by Frank Agbogbo and Mark Holtzapple at the ISAF XV conference at San Diego, Calif., USA Sep. 26-28, 2005, and in the article titled "Conversion of municipal solid waste to carboxylic acids using a mixed culture of mesophilic microorganisms", by Cateryna Aiello-Mazzarri, Frank K. Agbogbo and Mark T. Holtzapple, published in Bioresource Technology 97 (2006) pages 47-56, the so-called MixAlco process is described. In this process, biomass is first pretreated with lime, and then a mixed culture of acid-forming anaerobic microorganisms produces carboxylate salts.

These salts are subsequently concentrated and thermally converted to mixed ketones and finally hydrogenated to mixed alcohols.

Unfortunately, however, such mixed alcohols or mixed ketones cannot just be blended in with conventional fuels. The mixed ketones or mixed alcohols would alter properties of a conventional fuel, which may diminish the performance of such fuel and prevent it from being simply dropped in the existing fuel infrastructure for petroleum-derived fuels.

WO2010/053681 describes a biofuel production process comprising amongst others converting biomass to alcohol, and synthesizing a liquid hydrocarbon fuel from the alcohol. WO2010/053681 describes several processes for converting the biomass to alcohol. WO2010/053681 further mentions that alcohols may be directly oligomerized to hydrocarbons apparently in the absence of hydrogen at high temperatures (300-450° C.) and moderate pressures (1-40 atm.) in the presence of a zeolite catalyst in an oligomerization reactor (see also FIG. 10 of WO2010/053681). It is further indicated that by controlling the temperature and pressure of the oligomerization process and/or the composition of the zeolite, it is possible to direct the production of longer or shorter chain hydrocarbons. WO2010/053681 further mentions that it is also possible to control the amount of alkane branching in the final product. In its example 1, 27 tonnes of secondary alcohols are oligomerized at 350° C. at 10 atm. in the presence of zeolite catalyst and oxygen to produce 17 tonnes of gasoline and water. The alcohol to gasoline conversion apparently involves also a hydrogenation step. The approximate yield of gasoline based on weight of alcohol feed may be calculated to be approximately 63 wt %.

In its example 5, 27 tonnes of mixed ketones are converted to approximately 28 tonnes of secondary alcohols by hydrogenation over a nickel catalyst at approximately 130° C. and 15 atm hydrogen. The 28 tonnes of secondary alcohols are oligomerized at 350° C. at 10 atm. in the presence of zeolite catalyst to produce 12 tonnes of gasoline, 5 tonnes of light hydrocarbon residuals and 20 tonnes of water. The approximate yield of gasoline based on weight of alcohol feed may be calculated to be approximately 42 wt %.

In his thesis titled "TRANSFORMATION OF ACETONE AND ISOPROPANOL TO HYDROCARBONS USING HZSM-5 CATALYST", obtainable from the Office of Graduate Studies of the Texas A&M University, USA, (December 2009), S. T. Vasquez describes a transformation of acetone and isopropanol to hydrocarbons using a HZSM-5 catalyst. The thesis describes that zeolite solid-acid catalyst HZSM-5 can transform either alcohols or ketones into hydrocarbons. Catalysts having a silica to alumina molar ratio (SAR) of 80 and 280 were used. Vasquez suggests for further studies to modify the catalyst HZSM-5 with metals such as Nickel or Copper.

In the processes of WO2010/053681 and Vasquez, however, deactivation of the prior art catalysts may become an issue when the prior art processes would be applied on a commercial scale in a continuous manner. Without wishing to be bound by any kind of theory it is believed that operating the prior art processes for longer operating times may lead to excessive coking and subsequent deactivation of the catalysts.

For example Gayubo et al. in their article titled "Transformation of Oxygenate components of Biomass Pyrolysis Oil on a HZSM-5 Zeolite. I. Alcohols and Phenols", published in Ind. Eng. Chem. Res. 2004, vol 43, page 2610 to 2618 and their article titled "Transformation of Oxygenate Components of Biomass Pyrolysis Oil on a HZSM-5 Zeolite. II. Aldehydes, Ketones, and Acids" published in *Ind. Eng. Chem. Res.* 2004, 43, 2619-2626 describe the effects of temperature and space time on the transformation over a HZSM-5 zeolite catalyst of several model components of the liquid product obtained by the flash pyrolysis of vegetable biomass (1-propanol, 2-propanol, 1-butanol, 2-butanol, phenol and 2-methoxyphenol). The HZSM-5 zeolite catalyst comprised 30 wt % bentonite, 45 wt % fused alumina and 25 wt % of a HZSM-5 zeolite having a Silica to Alumina molar ratio of 24. They explain that the viability of transforming oxygenates into hydrocarbons was found to be limited by the catalyst deactivation by coke, and that this deactivation effects the product distribution with time on stream.

In addition, the processes of WO2010/053681 and Vasquez may not provide a smooth middle distillate boiling product that can easily be blended in with conventional fuels and/or that may simply be dropped in the existing fuel infrastructure for fossil-derived fuels.

It would be an advancement in the art to provide a process for converting a biomass material and/or a process for conversion of a feed containing one or more C3-C12 oxygenate(s) derived from a biomass material, which process can be operated for a prolonged period of time without substantial deactivation of the catalyst.

SUMMARY OF THE INVENTION

Advantageously the present invention provides a process for converting a biomass material comprising:
a) converting a biomass material in one or more steps into one or more C3-C12 oxygenates;
b) contacting the one or more C3-C12 oxygenates with hydrogen at a hydrogen partial pressure of more than 1.0 MegaPascal in the presence of a sulphided carbon-carbon coupling catalyst;
   wherein the carbon-carbon coupling catalyst comprises equal to or more than 60 wt % of a zeolite and in the range from equal to or more than 0.1 wt % to equal to or less than 10 wt % of a hydrogenation metal, based on the total weight of the carbon-carbon coupling catalyst.

It has now been found that such a process may advantageously allow for an extended catalyst stability against deactivation due to coke formation and/or due to catalyst poisoning.

Further such a process has been found suitable to produce a middle distillate boiling product. This middle distillate boiling product can be obtained in good yields and may advantageously be used in the production of biofuels and/or biochemicals. Advantageously this middle distillate boiling product may have a smooth boiling profile and/or may easily be blended in with conventional fuels and/or may simply be dropped in the existing fuel infrastructure for fossil-derived fuels.

By a middle distillate boiling product is herein preferably understood a product having a boiling point at 0.1 MegaPascal (MPa) in the range from equal to or more than 140° C. to equal to or less than 370° C. as determined by ASTM method D2887.

SUMMARY OF THE DRAWINGS

FIG. 1 illustrates a boiling point distribution as determined by ASTM method D2887 of two products obtainable by a process according to the invention.

DETAILED DESCRIPTION OF THE INVENTION

In step a) of the process according to the invention a biomass material is converted in one or more steps into one or more C3-C12 oxygenates.

The whole of the biomass material may be converted into such one or more C3-C12 oxygenates or a part of the biomass material may be converted into one or more C3-C12 oxygenates. In practice merely a part of the biomass material may be converted into one or more C3-C12 oxygenates, with the remainder of the biomass material being converted into other products.

In the embodiments of this invention the one or more C3-C12 oxygenates referred to preferably consist of one or more C3-C10 oxygenates and more preferably consist of one or more C3-C8 oxygenates.

By an oxygenate is herein understood a compound comprising at least one or more carbon atoms, at least one or more hydrogen atoms and at least one or more oxygen atoms. Examples of oxygenates include alkanols, ketones, aldehydes, carboxylic acids, ethers, esters and/or phenolic compounds.

In this invention the one or more oxygenates referred to preferably consist of one or more aldehydes, one or more ketones, one or more alkanols and/or combinations thereof. For example the one or more C3-C12 oxygenates are preferably oxygenates chosen from the group consisting of one or more C3-C12 aldehydes, one or more C3-C12 ketones, one or more C3-C12 alkanols and combinations thereof. More preferably the one or more oxygenates herein referred to consist of one or more alkanols, one or more ketones and/or combinations thereof. Most preferably the one or more oxygenates herein referred to consist of one or more ketones. For example, the one or more C3-C12 oxygenates referred to herein preferably consist of one or more C3-C12 ketones. The one or more C3-C12 oxygenates may therefore preferably comprise at least 50 wt %, more preferably at least 70 wt %, and most preferably at least 90 wt % of one or more C3-C12 ketones; more preferably at least 50 wt %, more preferably at least 70 wt %, and most preferably at least 90 wt % of one or more C3-C10 ketones; and most preferably at least 50 wt %, more preferably at least 70 wt %, and most preferably at least 90 wt % of one or more C3-C8 ketones.

By a "Cx"-oxygenate, -ketone, -aldehyde, -carboxylic acid, -ether, -ester or -alkanol is herein understood respectively an oxygenate, ketone, aldehyde, carboxylic acid, ether, ester or alkanol comprising x carbon atoms. By a "Cx-Cy"-oxygenate, -ketone, -aldehyde, -carboxylic acid, -ether, -ester or -alkanol is herein understood respectively an oxygenate, ketone, aldehyde, carboxylic acid, ether, ester or alkanol comprising in the range from equal to or more than "x" to equal to or less than "y" carbon atoms.

Examples of suitable alkanols include primary, secondary, linear, branched and/or cyclic alkanols, such as methanol, ethanol, 1-propanol, 2-propanol, 1-butanol, 2-butanol, pentanol, cyclopentanol, hexanol, cyclohexanol, 2-methyl-cyclopentanonol, heptanol, octanol, nonanol, decanol, undecanol, dodecanol, ethylene glycol, propylene glycol, 1,3-propanediol, butanediol, pentanediol, hexanediol, heptanediol, octanediol, nonanediol, decanediol, undecanediol, dodecanediol isomers thereof and/or mixtures thereof.

Examples of ketones include hydroxyketones, oxo-aldehydes, cyclic ketones and/or diketones, such as acetone, propanone, 2-oxopropanal, butanone, butane-2,3-dione, 3-hydroxybutane-2-one, pentanone, cyclopentanone, pentane-2,3-dione, pentane-2,4-dione, pentatrione, hexanone, hexane-2,3-dione, hexane-2,4-dione, hexane-2,5-dione, hexane-3,4-dione, hexane-triones, cyclohexanone, 2-methyl-cyclopentanone, heptanones, octanones, nonanones, decanones, undecanones, dodecanones, 2-oxopropanal, 2-oxo-butanal, 3-oxo-butanal, isomers thereof and/or mixtures thereof.

Examples of aldehydes include acetaldehyde, propionaldehyde, butyraldehyde, pentanal, hexanal, heptanal, octanal, nonal, decanal, undecanal, dodecanal, isomers thereof and/or mixtures thereof.

Examples of carboxylic acids include formic acid, acetic acid, propionic acid, butanoic acid, pentanoic acid, hexanoic acid, heptanoic acid, isomers thereof, and/or mixtures thereof.

Any ethers are preferably ethers with alkyl groups containing in the range from 1 to 6 carbon atoms. Examples of ethers include dimethyl ether, diethyl ether, methyl ethyl ether, diphenyl ether, methyl phenyl ether, ethyl phenyl ether, and/or mixtures thereof.

Any esters are preferably esters of carboxylic acids containing in the range from 2 to 6 carbon atoms and alcohols containing in the range from 1 to 4 carbon atoms. Examples of esters include methyl acetate, ethyl acetate, methyl propanoate, ethyl propanoate, methyl butanoate, ethyl butanoate and/or mixtures thereof.

The process according to the invention is further especially advantageous when the one or more C3-C12 oxygenates comprise a plurality of two or more C3-C12 oxygenates or more preferably when the one or more C3-C12 oxygenates comprise a plurality of three or more C3-C12 oxygenates. It has advantageously been found that even when a plurality of two or more distinctive C3-C12 oxygenates, or more preferably a plurality of three or more distinctive C3-C12 oxygenates, is fed to the process of the invention, still a middle distillate boiling product can be obtained that has a smooth boiling range distribution. By two or more distinctive oxygenates is herein for example understood two or more C3-C12 oxygenates comprising different numbers of carbon atoms.

As indicated above, the one or more C3-C12 oxygenates are derived from a biomass material. By a biomass material is herein preferably understood a material which contains bio-based carbon atoms as determined in ASTM method D6866-10 titled "Standard Test Methods for Determining the Biobased Content of Solid, Liquid and Gaseous samples using Radiocarbon Analysis". Examples of such biomass material include cellulosic material, lignocellulosic material, oils, fats and proteins. By a cellulosic material is herein preferably understood a material containing cellulose, and optionally lignin and/or hemicellulose. By a lignocellulosic material is herein preferably understood a material containing cellulose and lignin and optionally hemicellulose.

In a preferred embodiment the one or more C3-C12 oxygenates may at least partly be derived from a biomass material by means of fermentation. A wide range of biomass materials may be used as a starting point for the fermentation. Examples of suitable biomass materials include cellulose containing municipal wastes; food waste; agricultural wastes such as corn stover, soybean stover, corn cobs, rice straw, rice hulls, oat hulls, corn fibre, cereal straws such as wheat, barley, rye and oat straw; grasses; waste paper; sugar processing residues such as bagasse and beet pulp; and/or mixtures thereof.

The fermentation may be carried out with the help of one micro-organism or a mixture of two or more microorganisms. In a preferred embodiment the fermentation comprises fermenting the biomass material with a mixed culture of naturally occurring microorganisms, for example a mixed culture including microorganisms found in natural habitats such as the rumen of cattle, termite guts, and marine and terrestrial swamps to anaerobically digest biomass into a mixture of one or more oxygenates. In a further preferred embodiment fermentation comprises fermenting the biomass material with one or more marine microorganisms. In another further preferred embodiment the fermentation comprises fermenting the biomass material with one or more bacteria, preferably acid forming bacteria, most preferably clostridia or bacteria resembling clostridia. The fermentation may be carried out in an open or closed bioreactor but is preferably carried out in a closed bioreactor. Examples of suitable fermentation systems or bioreactors and methods therefore may include those found in U.S. Pat. No. 5,962,307, 5,874,263 and 6,262,313, herein incorporated by reference.

In an especially preferred embodiment the one or more C3-C12 oxygenates are chosen from the group consisting of one or more C3-C12 ketones, one or more C3-C12 alkanols or a combination thereof; and these C3-C12 ketones, C3-C12 alkanols or a combination thereof are obtained by a process comprising the steps of:
i) fermentation of a biomass material with one or more micro-organisms, preferably a mixture of two or more micro-organisms, to produce a fermentation broth comprising one or more carboxylic acids;
ii) neutralization of the one or more carboxylic acids with the help of a buffering agent to produce one or more carboxylate salts;
iii) transforming the one or more carboxylate salts into the one or more C3-C12 ketones, one or more C3-C12 alkanols or a combination thereof.

Preferences for the biomass material and the microorganisms are as described above.

The buffering agent in step ii) is preferably a carbonate salt, for example an ammonium carbonate, an alkali metal carbonate or an alkaline earth metal carbonate. More preferably the buffering agent in step ii) is chosen from the group consisting of ammonium bicarbonate, calcium carbonate and a combination thereof. Most preferably the buffering agent in step ii) is calcium carbonate and the produced one or more carboxylate salts are calcium carboxylate salts.

Optionally, steps i) and ii) may be combined, for example by carrying out the fermentation in step i) in the presence of a buffering agent to produce a fermentation broth comprising one or more carboxylate salts.

The transforming in step iii) may for example comprise heating the one or more carboxylate salts at a temperature in the range from equal to or more than 350° C. to equal to or less than 500° C. at a pressure of equal to or less than 0.05 MegaPascal to produce one or more C3-C12 ketones, optionally followed by a hydrogenation to produce one or more C3-C12 alkanols.

In a preferred embodiment the one or more carboxylate salts produced in step ii) are descummed and/or dewatered and/or dried before transforming in step iii). By descumming is herein preferably understood that cells and undigested solids are removed from the fermentation broth to produce an aqueous fermentation solution. By dewatering is herein preferably understood that water is removed from the fermentation broth or aqueous fermentation solution. Such a dewatering may for example be effected by means of vapor-compression evaporation. Drying may allow one to remove the remaining water left after dewatering and may allow one to precipitate the one or more carboxylate salts to create a biocrude or carboxylate salts. Such a dry biocrude or dry carboxylate salts may be less cumbersome and more energy efficient for transportation.

The effluent of transforming step iii) can optionally be further purified. For example, one or more C3-C12 ketones, one or more C3-C12 alkanols or a combination thereof, may optionally be separated from the remainder of the effluent of transforming step iii). Such a separation can be carried out in any manner known to the skilled person in the art.

In addition to the one or more C3-C12 oxygenates a feed into step b) of the process according to the invention may contain in the range from equal to or more than 150 to equal to or less than 2000 ppmw (parts per million by weight) sulphur and/or in the range from equal to or more than 300 to equal to or less than 5000 ppmw nitrogen. Such sulphur and/or nitrogen may suitably originate from the biomass material, for example from proteins, from which the one or more C3-C12 oxygenates are derived.

In the process according to the invention, in step b) the one or more C3-C12 oxygenates are contacted with hydrogen in the presence of a sulphided carbon-carbon coupling catalyst. The carbon-carbon coupling catalyst comprises equal to or more than 60 wt % of a zeolite and in the range from equal to or more than 0.1% wt to equal to or less than 10 wt % of a hydrogenation metal, based on the total weight of the carbon-carbon coupling catalyst. The zeolite preferably comprises 10-membered and/or 12-membered ring channels and a Silica to Alumina molar Ratio (SAR) in the range from equal to or more than 10 to equal to or less than 300. By a 10-membered and/or 12-membered ring channel is herein preferably understood a ring channel comprising 10 respectively 12 tetrahedral atoms (such as silicon or aluminium atoms) in the ring.

The carbon-carbon coupling catalyst according to the invention may herein below sometimes also be referred to as conversion catalyst. By a carbon-carbon coupling catalyst is herein preferably understood a catalyst that is capable of coupling two compounds, each of which compounds contains at least carbon and hydrogen, via a carbon-carbon bond under conditions suitable therefore. An example of a carbon-carbon coupling catalyst is a so-called oligomerization catalyst.

By a 10-membered respectively a 12-membered ring channel is herein preferably understood a channel defined by rings having 10 tetrahedral atoms respectively having 12 tetrahedral atoms in the ring. Examples of tetrahedral atoms include silicon and aluminium. The zeolite may contain 10-membered ring channels, 12-membered ring channels or a combination thereof. In addition to the 10-membered ring channels and/or 12-membered ring channels the zeolite may contain additional ring channels having a different number of tetrahedral atoms in the ring, preferably such additional ring channels are ring channels having less than 10 tetrahedral atoms in the ring.

The ring channels may for example be arranged in a one-dimensional, two-dimensional or three-dimensional network.

In one embodiment the zeolite is preferably a zeolite that has a Silica to Alumina molar Ratio (SAR) in the range from equal to or more than 10 to equal to or less than 100 before modification with a hydrogenation metal, and more preferably a zeolite that has a SAR in the range from equal to or more than 10 to equal to or less than 40 before modification with a hydrogenation metal. A carbon-carbon coupling catalyst with a zeolite having a SAR in these ranges before modification with a metal advantageously allows for improved stability of the catalyst towards deactivation. In addition the use of a carbon-carbon coupling catalyst with a zeolite having a SAR in these ranges may advantageously result in a good yield of so-called middle distillate boiling products.

Preferably the zeolite is a zeolite chosen from the group consisting of MFI-type zeolites, FER-type zeolites, BEA-type zeolites, MOR-type zeolites, FAU type zeolites and combinations thereof. By a certain type of zeolite, such as for example an MFI-type zeolite, is herein preferably understood a zeolite with a certain framework type, such as for example a zeolite with an MFI-framework type. These different zeolite framework types are for example defined in the "Atlas of Zeolite Framework types", sixth revised edition, published by Elsevier B. V. in 2007. Preferred examples of zeolites that can be comprised in the carbon-carbon coupling catalyst include ZSM-5, Mordenite zeolite, zeolite Beta, Y-zeolite or combinations thereof.

The carbon-carbon coupling catalyst further comprises a hydrogenation metal. The carbon-carbon coupling catalyst may comprise one or more hydrogenation metals. Preferably the carbon-carbon coupling catalyst comprises one or more hydrogenation metals chosen from the group consisting of copper, molybdenum, tungsten, cobalt and nickel. In addition the carbon-carbon coupling catalyst may comprise one or more other hydrogenation metals. More preferably the carbon-carbon coupling catalyst only contains hydrogenation metals chosen from the group consisting of nickel, cobalt, molybdenum, copper, tungsten and combinations thereof.

The carbon-carbon coupling catalyst preferably comprises in the range from equal to or more than 0.5 wt % to equal to or less than 10 wt % hydrogenation metal, based on the total weight of the carbon-carbon coupling catalyst. More preferably the carbon-carbon coupling catalyst comprises in the range from equal to or more than 0.5 wt % to equal to or less than 5 wt % of the hydrogenation metal, based on the total weight of the carbon-carbon coupling catalyst. Most preferably the carbon-carbon coupling catalyst comprises in the range from equal to or more than 1.0 wt % to equal to or less than 3.5 wt % of the hydrogenation metal, based on the total weight of the carbon-carbon coupling catalyst.

For practical purposes the weight percentages of hydrogenation metal and/or the zeolite as specified herein are best determined based on the total weight of the carbon-carbon coupling catalyst before sulphiding of the catalyst.

In addition to the zeolite and the hydrogenation metal, the carbon-carbon coupling catalyst may optionally comprise one or more binders and/or fillers. An example of a binder is silica sol. Examples of fillers include amorphous alumina, amorphous silica, or amorphous silica-alumina, boehmite alumina (AlOOH), natural or synthetic clays, pillared or delaminated clays, or mixtures of one or more of these. Examples of clays include kaolin, hectorite, sepiolite and attapulgite.

Preferably the carbon-carbon coupling catalyst comprises equal to or more than 70 wt %, more preferably equal to or more than 80 wt %, possibly even as high as equal to or more than 90 wt %, of the zeolite, based on the total weight of the carbon-carbon coupling catalyst. More preferably the carbon-carbon coupling catalyst comprises in the range from equal to or more than 60.0 wt % to equal to or less than 99.9 wt %, even more preferably in the range from equal to or more than 70.0 wt % to equal to or less than 95.0 wt %, still more preferably in the range from equal to or more than 70.0 wt % to equal to or less than 85.0 wt % of the zeolite, based on the total weight of the carbon-carbon coupling catalyst. The balance may consist of one or more hydrogenation metals and/or one or more binders and/or fillers.

The carbon-carbon coupling catalyst may be prepared in any manner known to be suitable to the skilled person in the art to prepare a catalyst comprising a zeolite and a hydrogenation metal as described above. For example the carbon-carbon coupling catalyst may be prepared by ion-exchange of the zeolite with an aqueous metal salt solution containing the hydrogenation metal; deposition of the hydrogenation metal on the zeolite by means of impregnation; and/or co-mulling of the zeolite and the hydrogenation metal.

The produced carbon-carbon coupling catalyst may subsequently be sulphided to produce the sulphided carbon-carbon coupling catalyst. Preferences for such sulphiding are described herein below.

In the process according to the invention, the one or more C3-C12 oxygenates are contacted with the sulphided carbon-carbon coupling catalyst in the presence of hydrogen at a hydrogen partial pressure of more than 1.0 MPa (Megapascal). Preferably the one or more C3-C12 oxygenates are contacted with the sulphided carbon-carbon coupling catalyst in the presence of hydrogen at a partial hydrogen pressure in the range from equal to or more than 2.0 MPa to equal to or less than 20.0 MPa, more preferably between 2.5 MPa to 18.0 MPa, even more preferably between 3.0 MPa and 15.0 MPa.

The hydrogen is preferably supplied as a hydrogen gas. Preferably the hydrogen is provided in the process according to the invention at a hydrogen to feed ratio (where the feed comprises the one or more C3-C12 oxygenates) in the range from equal to or more than 200 to equal to or less than 5000, more preferably in the range from equal to or more than 400 to equal to or less than 2500 Nl $H_2$/kg feed (normal liter hydrogen per kg feed, where a normal liter is understood to refer to a liter of gas at a pressure of 0.1 MPa (MegaPascal) and at a temperature of 20° C.)

Hence, in a continuous process, instead of or in addition to contacting the one or more C3-C12 oxygenates with the sulphided carbon-carbon coupling catalyst in the presence of hydrogen at a hydrogen partial pressure of more than 1.0 MPa, the one or more C3-C12 oxygenates may be contacted with the sulphided carbon-carbon coupling catalyst in the presence of hydrogen at a hydrogen to feed ratio in the range from equal to or more than 200 to equal to or less than 5000 Nl $H_2$/kg feed (where the feed comprises the one or more C3-C12 oxygenates).

Preferably the one or more C3-C12 oxygenates are contacted with the sulphided carbon-carbon coupling catalyst at a temperature in the range from equal to or more than 250° C. to equal to or less than 450° C., more preferably a temperature in the range from equal to or more than 280° C. to equal to or less than 380° C., even more preferably a temperature in the range from equal to or more than 320° C. to equal to or less than 370° C.

Preferably the one or more C3-C12 oxygenates are contacted with the sulphided carbon-carbon coupling catalyst at a Weight Hourly Space Velocity (WHSV) in the range from 0.2 to 2.5 kg feed per kg catalyst per hour.

By contacting the one or more C3-C12 oxygenates with hydrogen in the presence of the sulphided carbon-carbon coupling catalyst as described herein, a conversion product may be produced. This conversion product may herein also be referred to as carbon-carbon coupled product. By a carbon-carbon coupled product is understood a product containing one or more carbon-carbon coupled compounds. An example of a carbon-carbon coupled product is an oligomerization product. The conversion product may advantageously contain a middle distillate boiling product. Hence, after contacting the feed with the sulphided carbon-carbon coupling catalyst as described herein, advantageously a middle distillate boiling product may be produced. As indicated before, by a middle distillate boiling product is herein preferably understood a product having a boiling point at 0.1 MegaPascal (MPa) in the range from equal to or more than 140° C. to equal to or less than 370° C. as determined by ASTM method D2887. Examples of such middle distillate boiling products include kerosene/jet fuel range hydrocarbons and diesel range hydrocarbons. Suitably the conversion product may contain in the range from equal to or more than 30 wt %, more preferably equal to or more than 40 wt %, to equal to or less than 75 wt %, more preferably equal to or less than 65 wt %, of middle distillate boiling product. The remainder may be compounds having another boiling point.

The conversion product may suitably contain one or more carbon-carbon coupled compounds. By a "carbon-carbon coupled compound" is herein preferably understood a compound that has been obtained by coupling two other compounds via a carbon-carbon bond. Preferably the conversion product contains a mixture of hydrocarbon compounds. By a hydrocarbon compound is herein understood a compound containing at least carbon and hydrogen. Such a hydrocarbon compound may optionally also contain heteroatoms such as oxygen, sulphur or nitrogen. In one embodiment, the average molecular weight of the hydrocarbon compounds in the conversion product is higher than the average molecular weight of the hydrocarbon compounds in the feed. Preferably the conversion product contains one or more hydrocarbon compounds having in the range from equal to or more than 6 carbon atoms to equal to or less than 25 carbon atoms, preferably equal to or less than 18 carbon atoms.

The conversion product may comprise unsaturated, saturated, straight and/or branched hydrocarbon compounds. Further, the conversion product may still contain hydrocarbon compounds comprising heteroatoms such as oxygen, sulphur and/or nitrogen. In a preferred embodiment, the concentration of such heteroatoms in the conversion product is already reduced compared to the concentration thereof in the feed. In an especially preferred embodiment the conversion product contains already less than 100 ppmw or essentially no oxygen.

It may be considered advantageous to increase the saturation and/or the branching of the one or more hydrocarbon compounds in the conversion product and/or to reduce the content of oxygen, sulphur and/or nitrogen therein. And even when the conversion product contains less than 100 ppmw or essentially no oxygen, it may be still be considered advantageous to increase the saturation and/or the branching of the hydrocarbon compounds in the carbon-carbon coupled product.

In a preferred embodiment the process according to the invention therefore further comprises contacting the conversion product with hydrogen in the presence of a hydrotreating and/or hydroisomerization catalyst.

By a hydrotreating catalyst is preferably understood a catalyst that is capable of converting unsaturated carbon-carbon bonds into saturated carbon-carbon bonds and/or a catalyst that is capable of removing heteroatoms such as oxygen, nitrogen and sulphur. Preferably the hydrotreating catalyst is a hydrodeoxygenation catalyst, a hydrodesulphurization catalyst and/or a hydrodenitrogenation catalyst. By a hydroisomerization catalyst is preferably understood a catalyst that is capable of converting unbranched hydrocarbon compounds into branched hydrocarbon compounds and/or of converting mono-branched hydrocarbon compounds into multiple branched hydrocarbon compounds.

The hydrotreating and/or hydroisomerization catalyst can be any hydrotreating and/or hydroisomerization catalyst known to be suitable for the purpose of hydrotreating and/or hydroisomerization by the person skilled in the art. Preferably the hydrotreating catalyst and/or hydroisomerization catalyst are sulphided. Such sulfurization can be carried out as described herein below.

In one preferred embodiment the hydrotreating and/or hydroisomerization catalyst comprises, nickel or cobalt promoted, molybdenum or tungsten on a support. Examples of such catalysts include sulphided nickel-molybdenum on a support; sulphided cobalt-molybdenum on a support; sulphided nickel-tungsten on a support; and sulphided cobalt-tungsten on a support. The support preferably comprises a metal oxide, such as alumina, silica or silica alumina. Preferably the support contains in the range from equal to or more than 0wt % to equal to or less than 30 wt % of a zeolite; and/or in the range from equal to or more than 0 wt % to equal to or less than 50 wt % of amorphous silica, alumina or silica alumina. The remainder may be another filler and/or a binder. If the hydroisomerization and/or hydrotreating catalyst contains alumina, this alumina is preferably gamma-alumina.

In another preferred embodiment the hydrotreating and/or hydroisomerization catalyst may comprise phosphor. For example the hydrotreating and/or hydroisomerization catalyst may comprise nickel phosphide supported on alumina or carbon.

As a result of the hydrotreatment/hydroisomerization the percentage of saturated and/or branched hydrocarbon compounds in the conversion product may be increased; and/or the content of non-carbon, non-hydrogen atoms such as sulphur, nitrogen and/or oxygen in the conversion product may be reduced.

Any hydrotreatment and/or hydroisomerization is preferably carried out at a temperature in the range from 250° C. to 380° C.; a hydrogen partial pressure in the range from 1 to 15 MPa (MegaPascal); a Weight Hourly Space Velocity (WHSV) in the range from 0.2 kg liquid feed/(kg catalyst·hr) to 2.5 kg liquid feed/(kg catalyst·hr); and/or a hydrogen to liquid feed ratio in the range from 200 Nl hydrogen/kg liquid feed to 3000 Nl hydrogen/kg liquid feed (in this step the feed may be the liquid conversion product).

Preferably the weight ratio of sulphided carbon-carbon coupling catalyst to (preferably sulphided) hydrotreating catalyst and/or (preferably sulphided) hydroisomerization catalyst lies in the range from equal to or more than 1:1 to equal to or less than 4:1.

After hydrotreatment and/or hydroisomerization a hydrotreated and/or hydroisomerized conversion product may be obtained. Such hydrotreated and/or hydroisomerized conversion product may have an increased percentage of saturated and/or branched hydrocarbon compounds and/or a reduced content of non-carbon, non-hydrogen atoms such as sulphur, nitrogen and/or oxygen.

In a preferred embodiment the hydrotreated and/or hydroisomerized conversion product is a mixture containing one or more n-paraffinic, isoparaffinic, olefinic, naphthenic, and/or aromatic hydrocarbon compounds.

The content of olefinic hydrocarbon compounds in the hydrotreated and/or hydroisomerized conversion product preferably varies from equal to or more than 0 wt % to equal to or less than 10 wt %, based on the total weight of the hydrotreated and/or hydroisomerized conversion product.

The content of aromatic hydrocarbon compounds in the hydrotreated and/or hydroisomerized conversion product preferably varies from equal to or more than 0.1 wt % to equal to or less than 45 wt %, based on the total weight of the hydrotreated and/or hydroisomerized conversion product.

The content of naphthenic hydrocarbon compounds in the hydrotreated and/or hydroisomerized conversion product preferably varies from equal to or more than 0.1 wt % to equal to or less than 45 wt %, based on the total weight of the hydrotreated and/or hydroisomerized conversion product.

The content of n-paraffinic hydrocarbon compounds in the hydrotreated and/or hydroisomerized conversion product preferably varies from equal to or more than 0.5 wt % to equal to or less than 75 wt %, based on the total weight of the hydrotreated and/or hydroisomerized conversion product.

The content of isoparaffinic hydrocarbon compounds in the hydrotreated and/or hydroisomerized conversion product preferably varies from equal to or more than 0.5 wt % to equal to or less than 50 wt % (wt % refers to percentage by weight), based on the total weight of the hydrotreated and/or hydroisomerized conversion product.

In addition to carbon and hydrogen, the hydrotreated and/or hydroisomerized conversion product may contain other atoms such as sulfur, nitrogen and oxygen. However, the sulfur content of the hydrotreated and/or hydroisomerized conversion product is preferably reduced to a content of less than 100 ppmw, more preferably less than 10 ppmw. The nitrogen content of the hydrotreated and/or hydroisomerized conversion product is preferably reduced to a content less than 300 ppmw, and more preferably to less than 50 ppmw. The oxygen content of the hydrotreated and/or hydroisomerized conversion product is preferably reduced to a content of less than 2 wt %, preferably less than 0.5 wt %, and most preferably less than 0.2 wt %.

A middle distillate boiling product can conveniently be obtained from an, optionally hydrotreated and/or hydroisomerized, conversion product by any means known to be suitable by the person skilled in the art. Such means include for example fractionation, distillation and/or phase separation.

The process according to the invention may advantageously be used to prepare a plurality of hydrocarbon compounds that may be of use as a biofuel component and/or a biochemical component.

In a preferred embodiment therefore at least part of the, conversion product (obtained after contacting the feed with the sulphided carbon-carbon coupling catalyst) and/or at least part of the hydrotreated and/or hydroisomerized conversion product (obtained after further hydrotreatment and/or further hydroisomerization of such conversion product) is blended with one or more other components and used in a fuel. For example a, preferably hydrotreated and/or hydroisomerized, middle distillate boiling product may be blended with one or more additives to produce a biofuel.

The carbon-carbon coupling catalyst and optionally any hydrogenation catalyst and/or any hydrotreating catalyst and/or hydroisomerization catalyst may suitably be sulphided ex-situ (i.e. outside the process) or in-situ (i.e. during the process) or both to produce a sulphided carbon-carbon coupling catalyst, respectively a sulphided hydrogenation-, sulphided hydrotreating- and/or a sulphided hydroisomerization-catalyst.

In one preferred embodiment the respective catalyst(s) is/are sulphided by a liquid phase sulphiding procedure. In such a liquid phase sulphiding procedure the respective catalyst(s) is/are contacted with a liquid containing in the range from equal to or more 0.1 wt % to equal to or less than 3.5 wt % of sulphur, more preferably in the range from equal to or more than 1.5 wt % to equal to or less than 3.5 wt % of sulphur at a temperature in the range from equal to or more than 200° C. to equal to or less than 400° C., more preferably at a temperature in the range from equal to or more than 300° C. to equal to or less than 380° C., in the presence of hydrogen.

The sulphur-containing liquid can for example be the feed containing the one or more C3-C12 oxygenates, which may be spiked with sulphur, or for example another hydrocarbon containing liquid that additionally contains sulphur.

A preferred example of such a hydrocarbon containing liquid that additionally contains sulphur is a so-called straight run gasoil containing sulphur. Conveniently the liquid phase sulphiding with such a hydrocarbon containing liquid that additionally contains sulphur may be carried out in a reactor, where a catalyst is first sulphided in the reactor by contacting it with the hydrocarbon-containing liquid and subsequently the hydrocarbon-containing liquid is replaced by the feed comprising the one or more C3-C12 oxygenates.

In another preferred embodiment the respective catalyst(s) is/are sulphided by spiking the feed comprising the one or more C3-C12 oxygenates with sulphur containing compounds to produce a feed containing in the range from equal to or more than 0.1 wt % to equal to or less than 0.2 wt % sulphur and preferably maintaining this sulphur level throughout the process. Examples of such one or more sulphur containing compounds include dimethyldisulphide (DMDS) or SULFRZOL® 54 (SULFRZOL® 54 is a trademark, the sulphur containing compound is commercially available from Lubrizol).

In a further preferred embodiment sulphiding of the respective catalyst(s) can be accomplished by gas-phase sulphiding with a $H_2S/H_2$ mixture as the sulfiding medium. Such a $H_2S/H_2$ mixture preferably comprises in the range from 0.1 and 5 vol % $H_2S$ based on the total volume of the $H_2S/H_2$ mixture.

One skilled in the art will understand that a combination of the above preferred sulphiding embodiments is also possible.

In a preferred embodiment the sulphided catalyst(s) is/are kept in the sulphided state by carrying out the process in the presence of hydrogensulphide. The hydrogensulphide may be provided as such or may be generated in-situ by hydrogenation of the feed or a co-feed. In a preferred embodiment the hydrogensulphide may be generated by spiking the feed with one or more sulphur containing compounds. Preferably the feed may be spiked with an amount of sulphur in the range form equal to or more than 0.1 wt % to equal to or less than 0.2 wt %. Examples of such one or more sulphur containing compounds include dimethyldisulphide (DMDS) or SULFRZOL® 54 (SULFRZOL® 54 is a trademark, the sulphur containing compound is commercially available from Lubrizol).

The process according to the invention may for example be carried out as a batch process, a semi-batch process or a continuous process. Preferably the process according to the invention is a continuous process.

EXAMPLES

Examples 1a and 1b

Conversion of a Mixed Ketone Feed in a Stacked Bed Containing a Nickel-Exchanged Mordenite Zeolite Catalyst (Carbon-Carbon Coupling Catalyst A) and a Hydrotreatment Catalyst A powder of mordenite zeolite with an ammonium form and an SiO2:Al2O3 molar ratio (SAR) of approximately 20 was obtained commercially from Zeolyst International. An aqueous solution of 1 mol/liter nickel (II) nitrate hexahydrate was prepared and the pH of the solution was adjusted to 6 using ammonium hydroxide. The powder of mordenite zeolite was suspended in nickel nitrate solution in an amount of about 10 ml of nickel nitrate solution to about 1 gram of mordenite powder and the slurry was vigorously agitated using a stirrer or impeller to get a uniform suspension. Subsequently the temperature of the slurry was raised to 95° C. while refluxing and then maintained at 95° C. for 1 hour. The slurry was vigorously agitated using a stirrer or impeller during the whole of the ion-exchange step. Hereafter the slurry was cooled to 50° C., filtered to recover nickel-exchanged mordenite powder and washed with water.

The recovered nickel-exchanged mordenite powder was calcined at a temperature of 500° C. for 2 hours. Extrudates were prepared by mixing CATAPAL-D boehmite alumina (CATAPAL is a trademark, CATAPAL-D boehmite alumina is commercially obtainable from Sasol) in a ratio of 80 wt % nickel-exchanged Mordenite to 20 wt % alumina (80:20). The obtained extrudates were re-calcined at 500° C. during 2 hours. The prepared nickel-exchanged mordenite zeolite catalyst contained about 1.5 wt % nickel on the basis of the total weight of the catalyst (carbon-carbon coupling catalyst A).

The prepared 1.5 wt % nickel-exchanged mordenite zeolite catalyst (carbon-carbon coupling catalyst A) was loaded into a stacked bed configuration in a reactor.

The stacked bed configuration consisted of a top catalyst bed consisting of the carbon-carbon coupling catalyst A and a bottom catalyst bed comprising a nickel-molybdenum hydrotreating catalyst containing about 18 wt % molybdenum, about 6 wt % nickel and about 3 wt % phosphor on alumina (herein also referred to as 6Ni-18Mo/Al) in a weight ratio of carbon-carbon coupling catalyst A to nickel-molybdenum hydrotreating catalyst of about 1.95:1. In this configuration the top catalyst bed was located upstream of the bottom catalyst bed.

After the catalysts were loaded in the reactor, they were sulphided with a gasoil spiked with dimethyldisulphide (DMDS) to have a sulphur content of 2.5 wt % using a liquid phase sulphiding procedure by exposing the catalyst to the sulphur-containing gasoil and hydrogen at a temperature of about 345° C. for a period of about 12 hours at a pressure of 12 MPa.

After sulphiding of the catalysts, a feed containing a mixture of ketones having predominantly 3 to 11 carbon atoms as illustrated in table 1 (hereafter also referred to as "mixed ketone feed") was contacted with the catalysts at the conditions summarized in table 2 for examples 1a and 1b. The feed containing the mixture of ketones was derived from the fermentation of food waste (a mixture of animal and plant derived lignocellulosic biomass, proteins, fats and oils etc.). The mixed ketone feed had a total sulphur content of about 391 ppmw and a total nitrogen content of about 3350 ppmw, out of which the basic nitrogen content was about 914 ppmw. The mixed ketone feed was spiked with DMDS to increase its sulfur content to about 0.1% wt.

After contacting the mixed ketone feed with the catalysts, reactor effluent was collected.

A liquid hydrocarbon product was separated from the reactor effluent. Product characteristics for the liquid hydrocarbon product obtained are listed in table 3 for examples 1a and 1b.

In the below tables, the abbreviation "CCC cat." refers to the "carbon-carbon coupling catalyst"; and the abbreviation "HT cat." refers to the "hydrotreatment catalyst".

TABLE 1

| Mixed Ketone Feed Composition | |
|---|---|
| Component | Wt % |
| Acetone | 14.64 |
| 2-butanone | 18.19 |
| 3-butanone, 3-methyl | 0.90 |
| 2-pentanone | 22.53 |
| Methyl isobutyl ketone | 2.76 |
| 3-hexanone | 4.70 |
| 2-hexanone | 6.81 |
| 4-heptanone | 1.80 |

TABLE 1-continued

Mixed Ketone Feed Composition

| Component | Wt % |
|---|---|
| 3-heptanone | 1.42 |
| 2-heptanone | 4.18 |
| 4-octanone | 1.02 |
| 3-octanone | 0.84 |
| 2-octanone | 0.93 |
| 4-nonanone | 0.64 |
| 3-Nonanone | 0.22 |
| 2-Nonanone | 0.18 |
| 4-decanone | 0.18 |
| 3-decanone | 0.03 |
| 2-decanone | 0.07 |
| 6-undecanone | 0.08 |

Examples 2a and 2b

Conversion of a Mixed Ketone Feed in a Stacked Bed Containing a Cobalt-Exchanged Mordenite Zeolite Catalyst (Carbon-Carbon Coupling Catalyst B) and a Hydrotreatment Catalyst A powder of mordenite zeolite with an ammonium form and an SiO2:Al2O3 molar ratio (SAR) of approximately 20 was obtained commercially from Zeolyst International. An aqueous solution of 1 mol/liter cobalt (II) nitrate hexahydrate was prepared and the pH of the solution was adjusted to 6 using ammonium hydroxide. The powder of mordenite zeolite was suspended in cobalt nitrate solution in an amount of about 10 ml of cobalt nitrate solution to about 1 gram of mordenite powder and the slurry was vigorously agitated using a stirrer or impeller to get a uniform suspension. Subsequently the temperature of the slurry was raised to 95° C. while refluxing and then maintained at 95° C. for 1 hour. The slurry was vigorously agitated using a stirrer or impeller during the whole of the ion-exchange step. Hereafter the slurry was cooled to 50° C., filtered to recover cobalt-exchanged mordenite powder and washed with water.

The recovered cobalt-exchanged mordenite powder was calcined at a temperature of 500° C. for 2 hours. Extrudates were prepared by mixing CATAPAL-D boehmite alumina (CATAPAL is a trademark, CATAPAL-D boehmite alumina is commercially obtainable from Sasol) in a ratio of 80 wt % cobalt-exchanged mordenite to 20 wt % alumina (80:20). The obtained extrudates were re-calcined at 500° C. during 2 hours. The prepared cobalt-exchanged mordenite zeolite catalyst contained about 2 wt % cobalt on the basis of the total weight of the catalyst (carbon-carbon coupling catalyst B).

The prepared 2 wt % cobalt-exchanged mordenite zeolite catalyst (carbon-carbon coupling catalyst B) was loaded into a stacked bed configuration in a reactor. The stacked bed configuration consisted of a top catalyst bed consisting of the carbon-carbon coupling catalyst B and a bottom catalyst bed comprising the same nickel-molybdenum hydrotreating catalyst as used in examples 1a and 1b in a weight ratio of carbon-carbon coupling catalyst B to nickel-molybdenum hydrotreating catalyst of 1.87:1. The top catalyst bed was located upstream of the bottom catalyst bed.

After the catalysts were loaded in the reactor, they were sulphided with a gasoil spiked to have a sulphur content of 2.5 wt % using a liquid phase sulphiding procedure by exposing the catalyst to the sulphur-containing gasoil and hydrogen at a temperature of about 345° C. for a period of about 12 hours at a pressure of 12 MPa. Dimethyldisulphide (DMDS) was used to spike the gasoil with sulfur to obtain a sulfur content of 2.5 wt %.

After sulphiding of the catalysts, a feed identical to that in examples 1a and 1b, containing a mixture of ketones having predominantly 3 to 11 carbon atoms as illustrated in table 1, was contacted with the catalysts at the conditions summarized in table 2 for examples 2a and 2b.

After contacting the mixed ketone feed with the catalysts, reactor effluent was collected.

A liquid hydrocarbon product was separated from the reactor effluent. Product characteristics for the liquid hydrocarbon product obtained are listed in table 3 for examples 2a and 2b.

The boiling point distribution of the liquid hydrocarbon product obtained in example 2b (using a reaction temperature of 350° C.) was analyzed according to ASTM method D2887. The result is illustrated in FIG. 1. As can be seen in FIG. 1, the obtained boiling curve is smooth in the boiling range from 130° C. to 370° C. A smooth boiling point distribution, or lack of distinctive steps in such a boiling point distribution, is advantageous to achieve a suitable product specification (such as Jet A1 or JP8) for use in jet fuel.

Examples 3a and 3b

Conversion of a Mixed Ketone Feed in a Stacked Bed Containing a Nickel-Exchanged Zeolite Beta Catalyst (Carbon-Carbon Coupling Catalyst C) and a Hydrotreatment Catalyst A powder of zeolite Beta with an ammonium form and an SiO2:Al2O3 molar ratio (SAR) of approximately 20 was obtained commercially from Zeolyst International. An aqueous solution of 1 mol/liter nickel (II) nitrate hexahydrate was prepared and the pH of the solution was adjusted to 6 using ammonium hydroxide. The zeolite Beta powder was suspended in the nickel nitrate solution in an amount of about 10 ml of nickel nitrate solution to about 1 gram of zeolite Beta powder and the slurry was vigorously agitated using a stirrer or impeller to get a uniform suspension. Subsequently the temperature of the slurry was raised to 95° C. while refluxing and then maintained at 95° C. for 1 hour. The slurry was vigorously agitated using a stirrer or impeller during the whole of the ion-exchange step. Hereafter the slurry was cooled to 50° C., filtered to recover nickel-exchanged zeolite Beta powder and washed with water.

The recovered nickel-exchanged zeolite Beta powder was calcined at a temperature of 500° C. for 2 hours. Extrudates were prepared by mixing CATAPAL-D boehmite alumina (CATAPAL is a trademark, CATAPAL-D boehmite alumina is commercially obtainable from Sasol) in a ratio of 80 wt % nickel-exchanged zeolite Beta to 20 weight % alumina (80:20). The obtained extrudates were re-calcined at 500° C. during 2 hours. The prepared nickel-exchanged zeolite Beta catalyst contained about 1.8 wt % nickel on the basis of the total weight of the catalyst (carbon-carbon coupling catalyst C).

The prepared 1.8 wt % nickel-exchanged zeolite Beta catalyst (carbon-carbon coupling catalyst C) was loaded into a stacked bed configuration in a reactor. The stacked bed configuration consisted of a top catalyst bed consisting of the carbon-carbon coupling catalyst C and a bottom catalyst bed comprising the same nickel-molybdenum hydrotreating catalyst as used in examples 1a and 1b in a weight ratio of carbon-carbon coupling catalyst C to nickel-molybdenum hydrotreating catalyst of 1.59:1. The top catalyst bed was located upstream of the bottom catalyst bed.

After the catalysts were loaded in the reactor, they were sulphided with a gasoil spiked with dimethyldisulphide (DMDS) to have a sulphur content of 2.5 wt % using a liquid phase sulphiding procedure by exposing the catalyst to the sulphur-containing gasoil and hydrogen at a temperature of about 345° C. for a period of about 12 hours at a pressure of 12 MPa.

After sulphiding of the catalysts, a feed identical to that in examples 1a and 1b, containing a mixture of ketones having predominantly 3 to 11 carbon atoms as illustrated in table 1 was contacted with the catalysts at the conditions summarized in table 2 for examples 3a and 3b.

A liquid hydrocarbon product was separated from the reactor effluent. Product characteristics for the liquid hydrocarbon product obtained are listed in table 3 for examples 3a and 3b.

The boiling point distribution of the liquid hydrocarbon product obtained in example 3b (i.e. using a reaction temperature of 350° C.) was analyzed according to ASTM method D2887. The result is illustrated in FIG. 1. As can be seen in FIG. 1, the obtained boiling curve is smooth in the boiling range from 130° C. to 370° C.

A smooth boiling point distribution, or lack of distinctive steps in such a boiling point distribution, is advantageous to achieve suitable product specification (such as Jet A1 or JP8) for use in a jet fuel.

TABLE 2

Process Conditions for Examples 1a, 1b, 2a, 2b, 3a and 3b (All on a Single Pass Basis without any Gas or Liquid Recycle)

| Example | 1a | 1b | 2a | 2b | 3a | 3b |
|---|---|---|---|---|---|---|
| CCC cat. (SAR) | A (20) | A (20) | B (20) | B (20) | C (20) | C (20) |
| HT cat. | sulphided 6Ni—18Mo/Al | sulphided 6Ni—18Mo/Al | sulphided 6Ni—18Mo/Al | sulphided 6Ni—18Mo/Al | sulphided 6Ni—18Mo/Al | sulphided 6Ni—18Mo/Al |
| Weight ratio CCC cat.:HT cat. | 1.95:1 | 1.95:1 | 1.87:1 | 1.87:1 | 1.59:1 | 1.59:1 |
| WHSV CCC cat. (kg liquid feed/kg cat · hr) | 0.53 | 0.53 | 0.54 | 0.54 | 0.61 | 0.61 |
| WHSV HT cat. (kg liquid feed/kg cat · hr) | 1.03 | 1.03 | 1.01 | 1.01 | 0.97 | 0.97 |
| Temperature (° C.) | 300 | 350 | 300 | 350 | 300 | 350 |
| Pressure (MPa) | 12 | 12 | 12 | 12 | 12 | 12 |
| Hydrogen to feed ratio (Nl H2/kg feed) | 582 | 582 | 557 | 557 | 622 | 622 |

TABLE 3

Product Characteristics for the Liquid Hydrocarbon Product in Examples 1a, 1b, 2a, 2b, 3a and 3b

| Example | 1a | 1b | 2a | 2b | 3a | 3b |
|---|---|---|---|---|---|---|
| Oxygen content of the liquid hydrocarbon product (wt %) | 3.0 | 1.5 | 2.3 | 0.85 | <1.0 | 0.5 |
| Smooth boiling above (° C.) | 140 | 140 | 140 | 140 | 140 | 140 |
| 140° C.-370° C. boiling range fraction* (wt % based on weight of mixed ketone feed) | 15 | 23 | 15 | 21 | 17 | 23 |
| C5-140° C. boiling range fraction* (wt % based on weight of mixed ketone feed) | 55 | 48 | 53.5 | 47 | 53 | 48.5 |

*boiling fractions are based on ASTM D2887 SIMDIS method.

Example 4

Long Term Operation of a Process for the Conversion C3-C12 Ketones with the Help of a Sulphided Molybdenum-Exchanged Zeolite Beta Catalyst (Carbon-Carbon Coupling Catalyst D)

A molybdenum-exchanged zeolite Beta catalyst was prepared as follows: A 0.143 molar (mol/liter) solution of ammonium heptamolybdate tetrahydrate (equivalent to a molybdenum metal concentration of 1 Mol per liter) in water was prepared. The pH of this solution was adjusted to 6.0 using ammonium hydroxide. Zeolite Beta powder having a silica to alumina molar ratio ($SiO_2/Al_2O_3$ molar ratio) of approximately 20 in ammonium form and having a particle size distribution ranging from about 0.1 micrometer to about 5 micrometer was provided. A slurry of this powder in the ammonium heptamolybdate solution was prepared with a ratio of 10 mL of ammonium heptamolybdate solution per gram of zeolite powder to effect ion exchange. The slurry was heated to 95° C. under refluxing and was maintained at that temperature for a period of 1 hour allowing a molybdenum-exchanged zeolite Beta powder to be produced. After 1 hour, refluxing was stopped and the slurry was allowed to cool to about 50° C. and filtered. The filter cake containing the molybdenum-exchanged zeolite Beta powder was washed with water to remove any free molybdenum from the powder. The molybdenum-exchanged zeolite Beta powder was then dried at room temperature for about 16 hours. Subsequently it was dried at 130° C. for about 16 hours. The molybdenum-exchanged zeolite Beta was then calcined in air at 500° C. for 2 hours. The calcined molybdenum-exchanged zeolite Beta powder was shaped into extrudates using CATAPAL-D boehmite alumina (CATAPAL is a trademark, CATAPAL-D boehmite alumina is commercially obtainable from Sasol) as the binder. The weight ratio of zeolite powder to alumina in the extrudates was 80:20, corresponding to about 80 wt % of molybdenum-exchanged zeolite Beta in the extrudates. The extrudates were re-calcined in air at 500° C. for 2 hours to prepare a molybdenum exchanged zeolite Beta catalyst. The prepared molybdenum-exchanged zeolite Beta catalyst contained approximately 2.5 wt % Molybdenum on the basis of the total weight of the calcined catalyst (carbon-carbon coupling catalyst D).

The molybdenum-exchanged zeolite Beta catalyst (carbon-carbon coupling catalyst D) was used as a carbon-carbon coupling catalyst in a stacked bed configuration with a cobalt-molybdenum hydrotreatment catalyst comprising about 14 wt % molybdenum and about 3 wt % cobalt on an alumina support. The stacked bed consisted of a top bed containing the carbon-carbon coupling catalyst D (i.e. the molybdenum-exchanged zeolite Beta catalyst) and a bottom bed containing the hydrotreatment catalyst (i.e. the catalyst comprising cobalt and molybdenum on an alumina carrier). The volume ratio between the carbon-carbon coupling catalyst D and the hydrotreating catalyst was 82.5:17.5. The top catalyst bed was located upstream of the bottom catalyst bed.

After loading the catalysts into the stacked bed, both catalysts were subjected to a sulfidation treatment. The sulfidation was carried out by using a straight-run gasoil spiked with dimethyl disulfide (DMDS) to obtain an activation feed having 2.5 wt % elemental sulfur. After establishing a hydrogen flow of 250 Nl $H_2$/(lit cat·hr) and an activation feed flow of 0.50 lit liquid/(lit cat·hr), the reactor temperature was increased to 360° C. and held at that temperature until $H_2S$ levels in the off-gas stabilized. If so desired sulfidation of the catalyst can also be accomplished using gas-phase sulfidation with 5 vol % $H_2S/H_2$ mixture as the sulfiding medium, but this was not applied for this experiment.

To illustrate the stability of the sulphided molybdenum-exchanged zeolite Beta catalyst in the process of the invention, a long-term test was conducted where, in the presence of hydrogen, a mixed ketone feed having the composition as shown in table 1 was contacted with the carbon-carbon coupling catalyst (i.e. the sulphided molybdenum-exchanged zeolite Beta catalyst) in the top (first) catalyst bed and the hydrotreatment catalyst (i.e. the sulphided catalyst comprising cobalt and molybdenum on an alumina carrier) in the bottom (second) catalyst bed in a reactor. The mixed ketone feed was spiked with dimethyldisulphide (DMDS) such that it contained about 0.1 wt % (1000 ppmw) sulphur.

A step-wise program was applied where the reactor temperature was increased from 250° C. to 360° C. in steps while holding at each step for several days. The temperature was then reduced in steps to 320° C. The detailed conditions for the step-wise program are listed in table 4. During the temperature ramp-up, at 320° C. and a hydrogen partial pressure of 12 MegaPascal (condition C in table 4), a middle distillate product yield (defined as that part of the product boiling between 140° C. and 370° C. based on ASTM D2887) of 14-15 wt % was obtained after about 320 hours on stream. During the ramp-down, at the same temperature (condition G in table 4), after >700 hours on stream, middle distillate yield remained stable at 14-15 wt % even though a lower pressure of 6 MegaPascal was applied. Thus, the sulphided molybdenum-exchanged zeolite Beta catalyst continued to act as a carbon-carbon coupling catalyst after an extended time on stream.

Thus, the use of a catalyst as claimed in the current invention in combination with hydrogen partial pressures of more than 1.0 MegaPascal, more preferably more than 2.0 MegaPascal provides extended stability against deactivation due to coke formation and/or catalyst poisoning.

TABLE 4

Detailed Conditions for the Step-Wise Program in Example 4

| Condition | Temperature (° C.) | Hydrogen partial pressure (MPa) | WHSV (kg liq/lit cat. hr) | Hydrogen to liquid ratio (Nl $H_2$/kg feed) | product examined |
|---|---|---|---|---|---|
| A | 250 | 12.0 | 0.28 | 750 | |
| B | 280 | 12.0 | 0.28 | 750 | |
| C | 320 | 12.0 | 0.28 | 750 | x |
| D | 360 | 12.0 | 0.28 | 750 | |
| E | 360 | 8.0 | 0.28 | 750 | |
| F | 360 | 4.0 | 0.28 | 750 | |
| G | 320 | 5.8 | 0.28 | 750 | x |

Example 5

Conversion of a Mixed Feed of Ketones in a Stacked Bed Containing a Nickel-Impregnated Mordenite Zeolite Catalyst (Carbon-Carbon Coupling Catalyst E) and a Hydrotreatment Catalyst Extrudates were prepared by mixing mordenite zeolite (obtained from Zeolyst International), having a $SiO_2$ to $Al_2O_3$ molar ratio of approximately 20, with CATAPAL-D boehmite alumina (CATAPAL is a trademark, CATAPAL-D boehmite alumina is commercially obtainable from Sasol) as a binder in a ratio of 20 wt % alumina to 80 wt % mordenite zeolite. The extrudates containing 80 wt % mordenite zeolite bound with 20% CATAPAL-D boehmite alumina were impregnated with a Nickel (II) nitrate solution to obtain a nickel exchanged mordenite zeolite with a nickel loading of 0.9 wt %. The Nickel(II) nitrate was used as the nickel precursor. The impregnated extrudates were calcined at 500° C. to obtain a nickel-impregnated mordenite zeolite catalyst (carbon-carbon coupling catalyst E).

The prepared nickel-impregnated mordenite zeolite catalyst (carbon-carbon coupling catalyst E) was loaded into a stacked bed system as a top bed catalyst. The bottom catalyst bed of the stacked bed system contained a nickel-molybdenum hydrotreating catalyst containing about 18 wt % molybdenum, about 5 wt % nickel and about 3 wt % phosphor on an alumina support (herein also referred to as 5Ni-18Mo/Al). The volume ratio of carbon-carbon coupling catalyst to hydrotreating catalyst was 4:1, and the corresponding weight ratio was 2.7:1.

Subsequently the loaded carbon-carbon coupling catalyst E and the nickel-molybdenum hydrotreating catalyst were subjected to a liquid phase sulfidation treatment using a sulfidation feed. The sulfidation feed was a gasoil spiked with dimethyldisulphide (DMDS) to obtain a sulfur content of 2.5 wt % in the feed. Sulfidation was carried by flowing hydrogen and the sulfidation feed over the stacked bed catalyst system at a temperature of 320° C. and a pressure of 2.5 MegaPascal for a period of 4 hours.

After sulphiding of the catalysts, a feed containing a mixture of ketones having predominantly 3 to 10 carbon atoms as illustrated in table 5 was contacted with the catalysts at the conditions summarized in table 6 for example 5.

The feed containing the mixture of ketones was derived from the fermentation of food waste.

The sulfur content of this feed was about 500 ppmw. The feed was spiked with dimethyldisulphide (DMDS) to increase its sulfur content to about 1100 ppmw. The feed also had a total nitrogen content of about 1700 ppmw, out of which about 410 ppmw was basic nitrogen. The elemental oxygen content of the feed was measured to be about 20%.

TABLE 5

Mixed Ketone Feed used in Examples 5, 6 and 7

| Component | Wt % |
| --- | --- |
| Acetone | 12.8 |
| 2-Butanone | 11.3 |
| 2-Pentanone | 17.4 |
| Methyl isobutyl ketone | 1.6 |
| 2-Hexanone | 6.9 |
| 4-Heptanone | 1.1 |
| 3-Heptanone | 0.9 |
| 2-Heptanone | 10.8 |
| 4-Octanone | 1.3 |
| 3-Octanone | 2.0 |
| 2-Octanone | 2.6 |
| 4-Nonanone | 2.2 |
| 3-Nonanone | 0.5 |
| 2-Nonanone | 1.00 |
| 3-Decanone | 0.23 |

The processing of the feed was carried out over the stacked bed catalyst system at an average bed temperature of 341° C. and a reactor pressure of 12 MegaPascal. A hydrogen to liquid feed ratio of 1952 Nl H2/kg feed was used, and the space velocity with reference to the carbon-carbon coupling catalyst was 0.52 kg liquid feed/(kg catalyst·hr). The overall space velocity was 0.38 kg liquid feed/(kg catalyst·hr).

A two-layered product comprising an aqueous layer and an organic (hydrocarbon) layer was obtained.

The liquid hydrocarbon product (in this case consisting of the organic hydrocarbon layer) was separated from the reactor effluent. Product characteristics for the liquid hydrocarbon product obtained are listed in table 7 for example 5. The hydrocarbon liquid was analyzed for its boiling range using SIMDIS (ASTM D2887 method). The liquid hydrocarbon product fraction boiling between 140° C. and 370° C. may be suitable for use in a jet fuel and/or diesel after further distillation. The liquid hydrocarbon product fraction boiling between C5-140° C. may be suitable as a hydrocarbon boiling in the gasoline range.

Example 6

Conversion of a Mixed Feed of Ketones in a Stacked Bed Containing a Co-Mulled Nickel-Zeolite Beta Catalyst (Carbon-Carbon Coupling Catalyst F) and a Hydrotreatment Catalyst A carbon-carbon coupling catalyst was prepared by co-mulling as follows. Zeolite Beta powder in an ammonium form having an SiO2 to Al2O3 molar ratio of 25 was co-mulled with PURAL SB boehmite alumina (PURAL is a trademark, PURAL-SB boehmite alumina is commercially obtainable from Sasol) as a binder. The weight ratio of zeolite beta powder to the alumina binder was 4:1. During mulling, a nickel nitrate solution was added to achieve a nickel loading of 2 wt % on the final extrudate (corresponding to a 2.54 wt % nickeloxide (NiO) loading). The co-mulled material was extruded and the extrudates were calcined at a temperature of 500° C. to prepare the co-mulled nickel-zeolite beta catalyst (carbon-carbon coupling catalyst F).

The prepared co-mulled nickel-zeolite beta catalyst (carbon-carbon coupling catalyst F) was loaded into a stacked bed system as a top bed catalyst. The bottom catalyst bed of the stacked bed system contained a nickel-molybdenum hydrotreating catalyst containing about 18 wt % molybdenum, about 5 wt % nickel and about 3 wt % phosphor on an alumina support. The weight ration of carbon-carbon coupling catalyst F to nickel-molybdenum hydrotreating catalyst was 1.82:1

The catalyst system was subjected to a liquid phase sulfidation treatment using a sulfidation feed. The sulfidation feed was a gasoil spiked with dimethyldisulphide (DMDS) to obtain a sulfur content of 2.5 wt % in the feed. Sulfidation was carried by flowing hydrogen and the sulfidation feed over the stacked bed catalyst system at a temperature of 320° C. and a pressure of 2.5 MegaPascal for a period of 4 hours. Both catalyst systems were subjected to identical sulfidation treatment.

A mixed ketone feed as illustrated in table 5 was processed over the combination of carbon-carbon coupling catalyst F and nickel-molybdenum hydrotreatment catalyst at a temperature of 360° C. The reactor having a stacked bed catalyst configuration with the carbon-carbon coupling catalyst F at the top, and the hydrotreating catalyst at the bottom, was loaded with 510 mg of the carbon-carbon coupling catalyst and 280 mg of the hydrotreating catalyst. The mixed ketone feed flow to this reactor was 304 mg/hr, resulting in a weight hourly space velocity, based on carbon-carbon coupling catalyst, of 0.60 kg feed/(kg catalyst·hr), while that based on the hydrotreating catalyst was 1.08 kg feed/(kg catalyst·hr). Overall weight hourly space velocity for the stacked bed system was 0.39 kg feed/(kg total catalyst·hr).

The liquid hydrocarbon product was separated from the reactor effluent. Product characteristics for the liquid hydrocarbon product obtained are listed in table 7 for example 6.

Comparative Example 7

Conversion of a Mixed Feed of Ketones in Catalyst Bed Containing Only a Hydrotreatment Catalyst 1344 milligram (mg) of the hydrotreatment catalyst used in example 6 was subjected to a liquid phase sulfidation treatment using a sulfidation feed. The sulfidation feed was a gasoil spiked with dimethyldisulphide (DMDS) to obtain a sulfur content of 2.5 wt % in the feed. Sulfidation was carried by flowing hydrogen and the sulfidation feed over the catalyst at a temperature of 320° C. and a pressure of 2.5 MegaPascal for a period of 4 hours.

A mixed ketone feed as illustrated in table 5 was processed over the hydrotreatment catalyst at a temperature of 360° C. The mixed ketone feed flow was 330 mg/hr. Thus, in this example the reactor was operated with a weight hourly space velocity of 0.25 kg feed/(kg catalyst·hr).

The liquid hydrocarbon product (in this case consisting of the organic hydrocarbon layer) was separated from the reactor effluent. Product characteristics for the liquid hydrocarbon product obtained are listed in table 7 for comparative example 7.

As illustrated by example 6 and comparative example 7, the presence of a carbon-carbon coupling agent may increase the yield of middle distillate boiling hydrocarbons by about 100%.

Example 5 even shows an improvement in yield of middle distillate boiling hydrocarbons of about 170%, as compared to comparative example 7.

TABLE 6

Process Conditions for Examples 5, 6 and Comparative Example 7 (All on a Single Pass Basis without Any Gas or Liquid Recycle)

| Example | 5 | 6 | 7 (comparative) |
|---|---|---|---|
| CCC cat. (SAR) | E (20) | F | not applicable |
| weight of CCC cat. (mg) | — | 510 | not applicable |
| HT cat. | sulfided 5Ni—18Mo/Al | sulfided 5Ni—18Mo/Al | sulfided 5Ni—18Mo/Al |
| weight of HT cat. (mg) | — | 280 | 1344 |
| weight ratio CCC cat. to HT cat. | 2.7:1 | 1.82:1 | not applicable |
| WHSV CCC cat. (kg liquid feed/ kg cat. hr) | 0.52 | 0.60 | not applicable |
| WHSV HT cat. (kg liquid feed/ kg cat. hr) | 1.40 | 1.07 | 0.25 |
| temperature (° C.) | 340 | 360 | 360 |
| pressure (MegaPascal) | 12 | 2.5 | 2.5 |
| Hydrogen to mixed ketone feed ratio (Nl H2/kg feed) | 1952 | 2332 | 2126 |

"CCC cat." refers to the "carbon-carbon coupling catalyst"; and the abbreviation "HT cat." refers to the "hydrotreatment catalyst".

TABLE 7

Product Characteristics for the Liquid Hydrocarbon Product in Examples 5, 6 and Comparative Example 7

| Example | 5 | 6 | 7 (comparative) |
|---|---|---|---|
| Oxygen content of the liquid hydrocarbon product (wt %) | <0.2 | 0.23 | 0.1 |
| Smooth boiling above (° C.) | 150 | — | — |
| 140° C.-370° C. boiling range fraction* (wt % based on weight of ketone feed) | 21 | 15.51 | 7.75 |
| C5-140° C. boiling range fraction* (wt % based on weight of ketone feed) | 47 | — | — |

*boiling fractions are based on ASTM D2887 SIMDIS method.

That which is claimed is:

1. A process for converting a biomass material comprising
   a) converting at least a portion of the biomass material into one or more C3-C12 ketones, one or more C3-C12 alkanols or a combination thereof in steps comprising:
      i. fermenting the biomass material with one or more micro-organisms, to produce a fermentation broth comprising one or more carboxylic acids;
      ii. neutralizing the one or more carboxylic acids with the help of a buffering agent to produce one or more carboxylate salts; and
      iii. transforming the one or more carboxylate salts into the one or more C3-C12 ketones, one or more C3-C12 alkanols or a combination thereof
   b) contacting a feed comprising the one or more C3-C12 ketones, one or more C3-C12 alkanols or a combination thereof with hydrogen at a hydrogen partial pressure of more than 1.0 MegaPascal in the presence of a sulphided carbon-carbon coupling catalyst at a temperature in the range from equal to or more than 250° C. to equal to or less than 450° C. and at a WHSV in the range of from 0.2 to 2.5 kg feed per kg catalyst per hour; wherein the feed further comprises sulphur in the range from equal to or more than 150 to equal to or less than 2000 ppmw; and
   wherein the sulphided carbon-carbon coupling catalyst comprises equal to or more than 60 wt % of a zeolite and in the range from equal to or more than 0.1% wt to equal to or less than 10 wt % of a hydrogenation metal, based on the total weight of the sulphided carbon-carbon coupling catalyst.

2. The process according to claim 1, wherein the buffering agent in step ii) is calcium carbonate.

3. The process according to claim 2, wherein step iii) comprises heating the one or more carboxylate salts at a temperature in the range from equal to or more than 350° C. to equal to or less than 500° C. at a pressure of equal to or less than 0.05 MegaPascal to produce one or more C3-C12 ketones.

4. The process according to claim 3, wherein the produced C3-C12 ketones are hydrogenated to produce one or more C3-C12 alkanols.

5. The process according to claim 1, wherein the one or more carboxylate salts produced in step ii) are descummed and/or dewatered and/or dried before transforming in step iii).

6. The process according to claim 1, wherein the zeolite of the carbon-carbon coupling catalyst in step b) comprises 10-membered and/or 12-membered ring channels and a Silica to Alumina Molar Ratio (SAR) in the range from equal to or more than 10 to equal to or less than 300.

7. The process according to claim 1, wherein the sulphided carbon-carbon coupling catalyst in step b) is sulphided in-situ and/or ex-situ.

* * * * *